United States Patent [19]
Rivera et al.

[11] Patent Number: 5,512,835
[45] Date of Patent: Apr. 30, 1996

[54] ELECTRICAL PROBE AND METHOD FOR MEASURING GAPS AND OTHER DISCONTINUITIES IN ENCLOSURES USING ELECTRICAL INDUCTANCE FOR RF SHIELDING ASSESSMENT

[75] Inventors: Alexander F. Rivera, Hawthorne; Vincent Q. McElhaney, Oakland, both of Calif.

[73] Assignee: Hughes Aircraft Company, Los Angeles, Calif.

[21] Appl. No.: 994,815

[22] Filed: Dec. 22, 1992

[51] Int. Cl.⁶ .................................................. G01R 27/26
[52] U.S. Cl. ................................................ 324/654; 324/66
[58] Field of Search .............................. 324/654, 66, 67, 324/237

[56] References Cited

U.S. PATENT DOCUMENTS 5,041,786  8/1991  Takaishi et al. ............... 324/237 X
5,146,163  9/1992  Nawa ........................... 324/237 X

*Primary Examiner*—Kenneth A. Wieder
*Assistant Examiner*—Diep Do
*Attorney, Agent, or Firm*—Leonard A. Alkov; W. K. Denson-Low

[57] ABSTRACT

An apparatus (30) locates and measures any seam or other discontinuity (18) within a metal enclosure (10) by determining the characteristic inductance of the discontinuity. A pair of probes or electrodes (40, 42) are connected via a balun (46) to a network analyzer (56). When the probes are placed on either side of the discontinuity, the network analyzer can measure the length of the discontinuity by equating the discontinuity to an inductor.

4 Claims, 2 Drawing Sheets

FIG. 5.
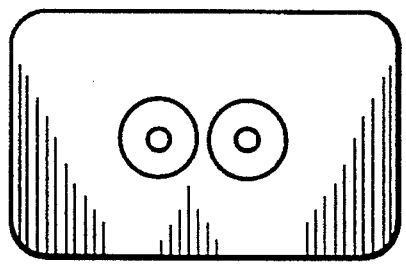
FIG. 6.
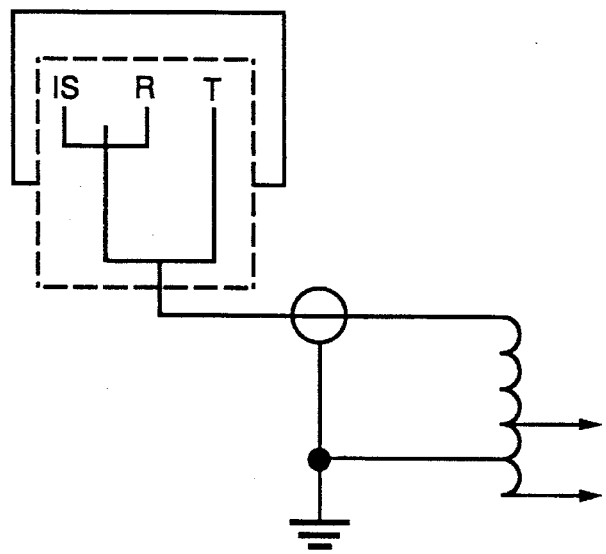
FIG. 7.
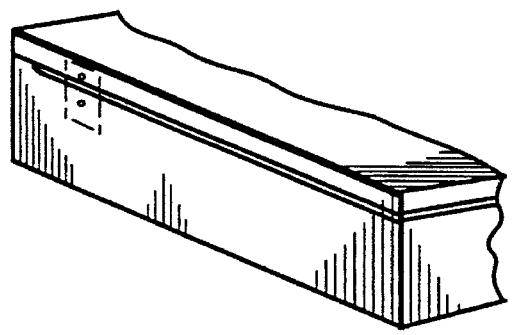
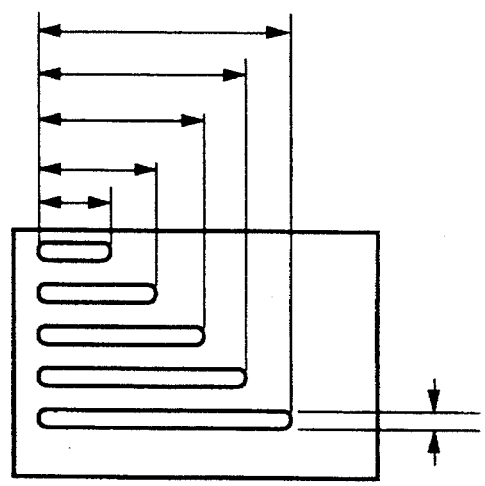
FIG. 8.

ELECTRICAL PROBE AND METHOD FOR MEASURING GAPS AND OTHER DISCONTINUITIES IN ENCLOSURES USING ELECTRICAL INDUCTANCE FOR RF SHIELDING ASSESSMENT

BACKGROUND OF THE INVENTION

1. Field of the Invention

The present invention relates to an apparatus and a method for measuring the length of such discontinuities as gaps, seams and cracks in electrically conductive parts or enclosures for determining their integrity with respect to such phenomena as radio frequency (RF) leakage and to mechanical strength characteristics.

2. Description of Related Art and Other Considerations

To secure electronic equipment from exterior electromagnetic radiation which could deleteriously affect its performance, such electronic equipment is conventionally packaged in a radiation secure enclosure. Conversely, it may also be necessary to protect the environment external to the electronic equipment from radiation generated from within the enclosure. Therefore, the enclosure must define a radiation secure environment. Such security is weakened by the presence of any discontinuities in the enclosure, such as slots, cracks, and open seams which will permit electromagnetic radiation to enter into or exit from the enclosure. It is, therefore, necessary to determine if such discontinuities exist and, if so, to locate and measure them.

Conventionally, enclosures have been tested by use of such instrumentation as time domain reflectometers, milliohm meters, devices employing magnaflux powders, feeler gages and transfer impedance measurement mechanisms. All of these instrumentation or techniques have one or more deficiencies.

The time domain reflectometer is a high band width instrument which obtains measurements at such high frequencies as to make the measurements susceptible to stray capacitance, which detracts from the accuracy of the test results. It is further a relatively expensive apparatus.

The milliohm meter cannot localize current paths and, therefore, is incapable of identifying the location of a gap or discontinuity. It only states that a gap exists, and then only if the gap is large.

In the magnaflux technique, ferromagnetic powder is placed on the enclosure to be tested, through which a large or high current is passed. The use of a high current requires that the enclosure have large paint-free contact areas. If such areas were previously painted, they would have to be later painted. This ferromagnetic powder also presents a potential contamination problem in that any residual powder must be removed. In addition, the high current utilized in the testing process poses safety problems.

Feeler gages constitute precisely dimensioned pieces of metal or the like, one or more of which is pushed into a suspected gap. Such gages are effective only on relatively large gaps and are ineffective if the gaps are not linear. Furthermore, the use of such a mechanical device creates a hazard of producing a gap in the enclosure where none had previously existed.

Transfer impedance measurement requires the use of microwave equipment and custom test jigs for each article. It cannot locate the gap, but only identifies if one exists. Further, it is not amenable to use in the field because it requires a shielded room.

Therefore, existing instrumentation and techniques have been found to be less than fully useful.

SUMMARY OF THE INVENTION

These and other problems are successfully addressed and overcome by the present invention. Briefly, the present invention comprises method and apparatus for inspecting an electrically conductive device or part to measure any discontinuity therein through the determination of the characteristic inductance of the discontinuity.

More specifically, a pair of probe tips or electrodes are connected by a balun to a network analyzer. The probe tips, which are placed on either side of a seam or other discontinuity in a metal enclosure, for example, enables the network analyzer to measure the length of the discontinuity by equating the discontinuity to an inductor.

Several advantages are derived from this arrangement. Because the length of the discontinuity is the vital factor in determining RF leakage and enclosure integrity, the novelty and utility of the present invention is predicated upon its ability to measure displacements much smaller than the wavelength of the frequency used. Because a network analyzer is able to measure minute changes in phase, this ability is used to advantage to relate these phase changes to changes in displacement. Measurement of displacements at low frequency allows the characteristic impedance and stray capacitance of the seam to be ignored with preference to its length. The small device embodied by the present invention utilizes inexpensive, low band width components, and is easily manufactured. It is non-contaminating and, therefore, preferred over any conventional equipment which requires the use of potentially contaminating powders. It is insensitive to stray capacitances at higher frequencies, and provides more accurate data than, for example, a time domain reflectometer. It is not physically inserted into the discontinuity, so that non-linear portions of the discontinuity will not restrict the use of the present invention. It can also be used to verify the tightness of enclosure covers or to identify the need for additional cover fasteners. It is non-destructive to the part being tested.

Other aims and advantages, as well as a more complete understanding of the present invention, will appear from the following explanation of an exemplary embodiment and the accompanying drawings thereof.

BRIEF DESCRIPTION OF THE DRAWINGS

FIG. 5 is a bottom view of the apparatus illustrated in FIG. 4, showing its electrode probes;

FIG. 6 is a circuit diagram of the electrical circuit in the apparatus depicted in FIG. 4;

FIG. 7 illustrates the use of the apparatus, shown in phantom, with its electrodes or probes placed against the FIG. 1 enclosure to circumscribe its gap; and FIG. 8 is a view of a test plate used for purposes of calibration and experimental testing of the present invention.

DETAILED DESCRIPTION OF THE PREFERRED EMBODIMENTS

Figure 1:
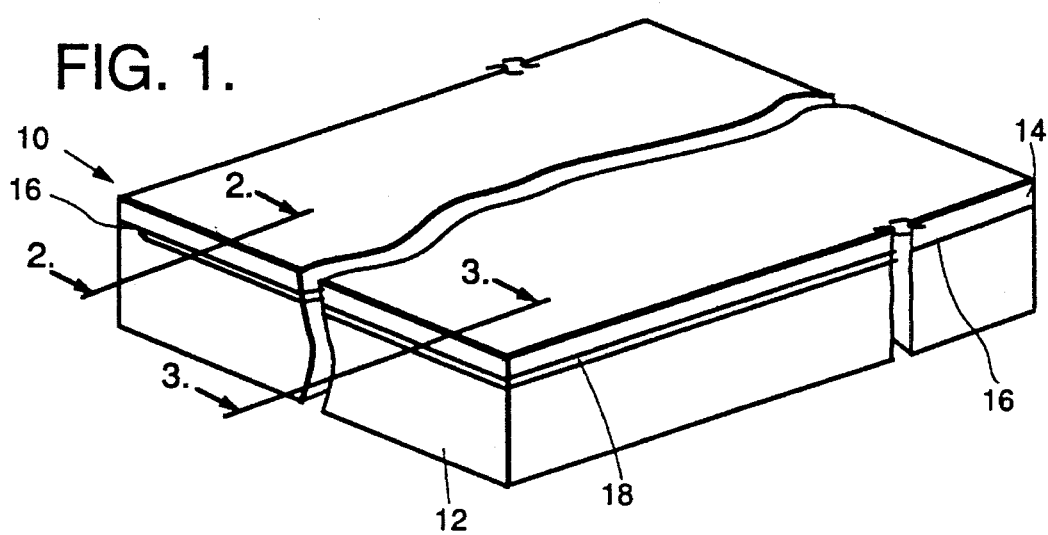
FIG. 1 is a perspective view of an enclosure having a gap or other discontinuity which is capable of being probed and measured by use of the present invention.
Figure 2:
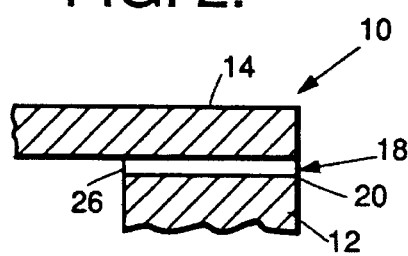
FIG. 2 is a cross-section of the enclosure depicted in FIG. 1 taken along line 2—2 thereof.
Figure 3:
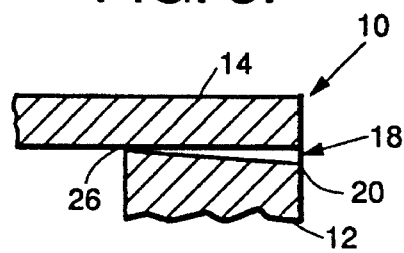
FIG. 3 is a cross-section of the enclosure illustrated in FIG. 1 taken along line 3—3 thereof.

Shown in FIGS. 1-3 is an enclosure 10, which houses electronic components or apparatus in a secure manner so as to isolate the apparatus from exterior electromagnetic radiation, or to protect any electromagnetic radiation generated by the apparatus from escaping from enclosure 10. Thus, enclosure 10 is constructed of an electrically conductive material, generally of metal or, at least, of walls having metallic foil completely placed or laminated to their surfaces.

Enclosure 10 includes a base 12 for receiving the electronic equipment and a lid 14 which is sealed to base 12. To effect a sealed, electrically safe enclosure, lid 14 should be completely sealed to base 12 at all intersecting points or surfaces 16. Because of imperfections, contact between the base and the lid is not complete between all of their intersecting peripheral surfaces, and discontinuities 18 exist in some of the intersecting points 16. Such discontinuities 18 may extend throughout the entire intersection from the exterior of enclosure 10 at point 20 to its interior at point 22, as shown in FIG. 2, so that there is a space extending completely from exterior point 20 of the intersection as well as interior point 22. The discontinuity shown in FIG. 3, however, may comprise a spaced discontinuity at its exterior at point 24 but contact at the interior portion, as designated by indicium 26. It is further obvious that such contact at portion 26 may be at one or more points between the interior and exterior of the enclosure.

It is such discontinuities that cause radio frequency (RF) leakage and detracts from the integrity of the enclosure. It is necessary to test enclosure 10 for such discontinuities, not only to locate them but to determine their lengths.

Figure 4:
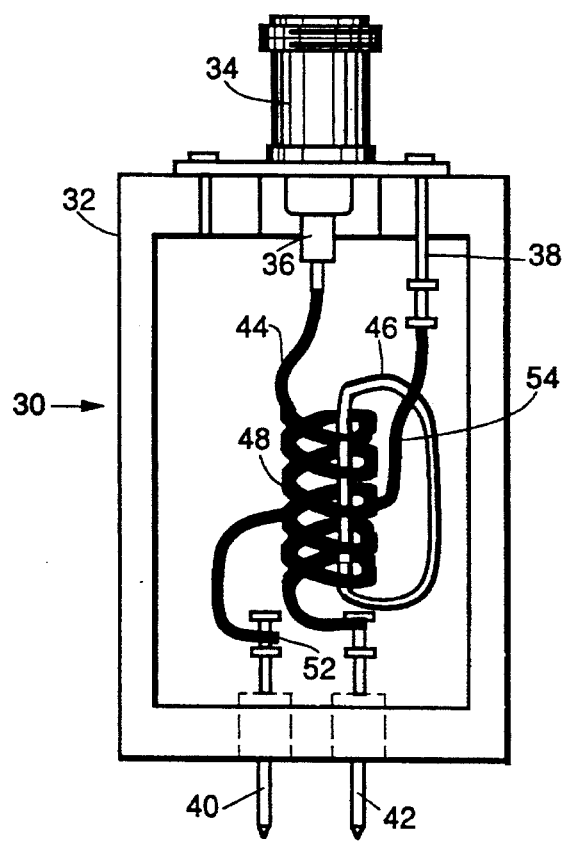
FIG. 4 is a view of electrical apparatus embodying the present invention, to identify and measure gaps and other discontinuities in such enclosures as are shown in FIG. 1.

Such discontinuities can be measured by use of an apparatus 30, shown in FIG. 4, comprising a housing 32 enclosing electronic components. In connection with FIG. 4 and as more particularly depicted in FIG. 6, A BNC (bayonet Navy connector) 34 or other suitable connector is secured to one end of the housing and includes a pair of terminals 36 and 38 which extend into the interior of housing 32. A pair of probes or electrodes 40 and 42 are secured to an opposite end of housing 32 and extend through a wall of the end from the exterior to the interior of the housing. Terminal 36 is connected to probe 42 by a winding 44, which is wound for several turns about a an element 46 of material having magnetic properties, which constitutes a balun (balanced-to-unbalanced transformer), consisting of windings 48 and 50 and element 46. Winding 44 is divided into a pair of segments 48 and 50 which, for illustrative purposes, are formed so that winding segment 48 has more turns about element 46 than winding segment 50. Segments 48 and 50 are defined by means of a lead 52 which is connected to and extends from an intermediary portion of winding 44 to probe 40. Also refer to FIG. 6 for this configuration. Another lead 54 extends from terminal 38 and is coupled to a portion of winding segment 50 adjacent to the point at which lead 52 is secured to winding 44. The electrical arrangement depicted in FIG. 4 is schematically depicted in FIG. 6, and further discloses a coupling of BNC connector 34 to a network analyzer 56 of conventional construction.

Use of apparatus 30 is illustrated in FIG. 7. Probes 40 and 42 of apparatus 30 are positioned on either side of intersection 16 so that the probes bridge the intersection. The inductance of discontinuity 18 is displayed on network analyzer 56 when probes 40 and 42 contact the enclosure 10 across the width of the discontinuity. The length of discontinuity 18, which is being determined, is proportional to the inductance, as measured by the network analyzer 56, which typically measures electrical inductance, with use of probes 40 and 42. Consequently, the measurement by the network analyzer is carried out as an inductance measurement; the inductance measurement is then equated to length of discontinuity 18. This relationship is more specifically set forth below.

Initial slot inductance calculations were made by use of a test piece or plate 58 shown in FIG. 8. Test piece 58 simulated a slotted enclosure wall, and includes several slots 60–68 therein, measuring respectively 1.0 centimeters, 2.0 centimeters, 3.0 centimeters, 4.0 centimeters and 5.0 centimeters, all with widths of 0.64 centimeters. Initial slot inductance calculations predicted an inductance of 0.83 nH/cm (nano Henrys per centimeter). This calculated inductance constant was accurate for slots as narrow as 10 E-6 meters. The slots equally represented gaps or open seams. Because the measured inductance is not a function of slot width, the standard width of 0.64 centimeters was selected. Network analyzer 56 was triggered to display the inductance after probes 40 and 42 of apparatus 30 were pressed into test plate 58 bridging one of the slots.

Theoretical inductance value versus slot length were tabulated as shown in the below table along with the measured inductance values.

| Length cm | Measured nH* | Theory nH |
|---|---|---|
| 0 | 0 | 0 |
| 1 | 0.5 | 0.8 |
| 2 | 1.3 | 1.7 |
| 3 | 2.2 | 2.5 |
| 4 | 3.6 | 3.3 |
| 5 | 5.0 | 4.2 |

*The resolution of the 1 cm test is on the order of 1 mm @ 10 MHz.

Although the invention has been described with respect to a particular embodiment thereof, it should be realized that various changes and modifications may be made therein without departing from the spirit and scope of the invention.

What is claimed is:

1. A method for inspecting an electrically conductive device, structure or mechanical component to measure the length of a discontinuity therein, comprising the steps of:

placing electrical probes about the discontinuity;

coupling the probes to a balun;

coupling the balun to a network analyzer;

measuring a value of characteristic inductance of the discontinuity with the network analyzer; and evaluating the length of the discontinuity using the value of the characteristic inductance of the discontinuity as measured by the network analyzer in accordance with a predetermined relationship of substantially 0.83 nano Henrys per centimeter between the characteristic inductance of the discontinuity and the length of the discontinuity.

2. Apparatus for inspecting an electrically conductive device for measuring the length of a discontinuity therein, comprising:

electrical probes placed about the discontinuity;

a balun connected to said electrical probes;

a network analyzer coupled to said balun, wherein said network analyzer measures the value of characteristic inductance of the discontinuity; and means for evaluating the length of the discontinuity using the value of the characteristic inductance of the discontinuity as measured by the network analyzer in accordance with a predetermined relationship between the length of the discontinuity and the characteristic inductance value.

3. The apparatus of claim 2 for inspecting an electrically conductive device wherein said relationship between the characteristic inductance value and the length of the discontinuity is substantially 0.83 nano Henrys induction per centimeter of discontinuity.

4. The apparatus of claim 2 for inspecting an electrically conductive device wherein said relationship between the length of the discontinuity and the characteristic inductance is set forth as follows:

| characteristic inductance (nano Henrys) | length of the discontinuity (length in centimeters) |
| --- | --- |
| 0 | 0 |
| 0.5 | 1 |
| 1.3 | 2 |
| 2.2 | 3 |
| 3.6 | 4 |
| 5.0 | 5 |

\* \* \* \* \*